(12) United States Patent
Joo et al.

(10) Patent No.: US 8,329,791 B2
(45) Date of Patent: Dec. 11, 2012

(54) PHOSPHONATE COMPOUND AND FLAME RETARDANT STYRENIC RESIN COMPOSITION INCLUDING THE SAME

(75) Inventors: Beom Jun Joo, Seoul-si (KR); Man Suk Kim, Seongnam-si (KR); Woo Joong Kim, Anyang-si (KR); Seon Ae Lee, Seoul-si (KR); Byun Kun Lee, Gunpo-si (KR); Myoung Jun Kim, Hwaseong-si (KR)

(73) Assignee: Cheil Industries Inc., Gumi-si (KR)

( * ) Notice: Subject to any disclaimer, the term of this patent is extended or adjusted under 35 U.S.C. 154(b) by 0 days.

(21) Appl. No.: 13/166,156

(22) Filed: Jun. 22, 2011

(65) Prior Publication Data
US 2011/0251313 A1    Oct. 13, 2011

Related U.S. Application Data

(63) Continuation-in-part of application No. PCT/KR2009/004106, filed on Jul. 23, 2009.

(30) Foreign Application Priority Data

Dec. 26, 2008  (KR) .................. 10-2008-0134763

(51) Int. Cl.
C08K 5/49    (2006.01)
C08K 5/52    (2006.01)
(52) U.S. Cl. ...................... 524/115; 524/127
(58) Field of Classification Search .................. 524/115
See application file for complete search history.

(56) References Cited

U.S. PATENT DOCUMENTS 6,028,130 A    2/2000  Weber et al.
6,388,046 B1   5/2002  Campbell et al.
6,956,073 B2  10/2005  Takagi et al.
2003/0162870 A1  8/2003  Kimura et al.
2006/0138391 A1  6/2006  Drewes et al.
2008/0227884 A1  9/2008  Mineo et al.
2010/0093928 A1  4/2010  Yokoyama et al.
2010/0108368 A1  5/2010  Sato et al.

FOREIGN PATENT DOCUMENTS

| KR | 10-2003-0032873 | 4/2003 |
| KR | 10-2004-0062428 | 7/2004 |
| KR | 10-2005-0069467 | 7/2005 |
| WO | 2008/108485 A1 | 9/2008 |
| WO | 2008/114858 A1 | 9/2008 |
| WO | 2010/074384 A1 | 7/2010 |

OTHER PUBLICATIONS

Naga Raju et al., Magnetic Resonance in Chemistry, vol. 28, 908-917, 1990.*
Bicak et al., "Removal of Transition Metal Cations and Their Counteranions by Crosslinked Epoxy—Amine Polymer," Journal of Applied Polymer Science, 1998, vol. 68, pp. 103-109.
International Search Report in counterpart International Application No. PCT/KR2009/004106 dated Feb. 18, 2010, pp. 1-6.

* cited by examiner

Primary Examiner — Hui Chin
(74) Attorney, Agent, or Firm — Summa, Additon & Ashe, P.A.

(57) ABSTRACT

The present invention provides phosphonate compounds represented by Chemical Formula 1. In addition, the invention provides flame retardant styrene resin compositions comprising (A) styrene resin, (B) polyphenylene ether resin, and (C) the phosphonate compound. The flame retardant styrene resin compositions according to the invention: can provide protection against fire, exhibit improved impact strength, and can be environment-friendly.

13 Claims, 2 Drawing Sheets

PHOSPHONATE COMPOUND AND FLAME RETARDANT STYRENIC RESIN COMPOSITION INCLUDING THE SAME

CROSS-REFERENCE TO RELATED APPLICATIONS

This application is a continuation-in-part of International Application No. PCT/KR2009/004106, filed Jul. 23, 2009, pending, which designates the U.S., published as WO 2010/074384, and is incorporated herein by reference in its entirety, and claims priority therefrom under 35 USC Section 120. This application also claims priority under 35 USC Section 119 from Korean Patent Application No. 10-2008-0134763, filed Dec. 26, 2008, in the Korean Intellectual Property Office, the entire disclosure of which is also incorporated herein by reference.

FIELD OF THE INVENTION

The present invention relates to a novel phosphonate based compound and a flame retardant styrenic resin composition including the same.

BACKGROUND OF THE INVENTION

Generally, styrenic resins have good processability and mechanical properties and have accordingly been used to produce housing parts for many electrical and electronic goods. However, styrenic resins can be readily ignited and further can readily spread fire. Moreover, styrenic resins are subject to various mandatory controls on flammability for safety reasons in countries such as the United States, Japan and Europe, and are required to have high flame retardancy to meet the Underwriter's Laboratories Standard for use in the housings of electrical and electronic appliances.

A widely used and known method for imparting good flame retardancy to styrenic resin comprises adding a halogen-containing compound as a flame retardant to a rubber-modified styrenic resin and adding an antimony-containing compound as a flame retardant aid. Examples of halogen-containing compounds used to impart flame retardancy include polybromodiphenyl ether, tetrabromobisphenol-A, epoxy compounds substituted with bromine, chlorinated polyethylene, and the like. Antimony trioxide or antimony pentaoxide is commonly used as an antimony-containing compound.

When a halogen- and antimony-containing compound is used to improve flame retardancy of resins, a desired degree of flame retardancy can readily be imparted to the resulting products without significantly degrading the physical properties thereof. However, hydrogen halide gases released by halogen-containing compounds during processing can have fatal effects on the human body. Particularly, polybromodiphenyl ether, which is widely used as a halogen-containing flame retardant, may produce toxic gases such as dioxin or furan during combustion. Accordingly, there is a need to develop flame retardancy methods that do not employ halogen-containing compounds.

Rubber-modified styrenic resins generally have little remaining char during combustion, and thus it is hard to impart flame retardancy to such resins in their solid state (Journal of Applied Polymer Science, 1998, vol. 68, p. 106). Therefore, it may be necessary to add a char forming agent to a rubber-modified styrenic resin so that char can be formed in order to obtain desirable flame retardancy.

A well known and widely used method of imparting flame retardancy without using halogen-containing flame retardants uses a phosphate ester flame retardant. However, relatively high amounts of phosphate ester flame retardants or flame retardant aids are required to obtain sufficient flame retardancy, which can negatively impart other properties of the resin.

WO 2008/114858, WO 2008/108485 and US 2008/0227884 refer to 9,10-dihydro-9-oxa-10-phosphaphenanthrene-10-oxide, which is a phosphonate based cyclic compound, and a reactive flame retardant resin using the same. However, 9,10-dihydro-9-oxa-10-phosphaphenanthrene-10-oxide is only used as a phosphorous-containing flame retardant hardener for imparting flame retardancy to thermoset (crosslinked and hardened) resins.

SUMMARY OF THE INVENTION

The present invention provides a novel phosphonate based compound which can be added to a resin composition to provide flame resistance.

The present invention further provides a flame resistant styrenic resin composition including a novel phosphonate based compound which can have fire stability.

The present invention further provides an environmentally-friendly styrenic resin composition which includes a halogen-free flame retardant and which can have excellent flame resistance as compared to a composition including a phosphate ester flame retardant.

Other aspects and advantages of this invention will be apparent from the ensuing disclosure and appended claims.

The present invention provides a phosphonate based compound represented by the following Chemical Formula 1.

[Chemical Formula 1]

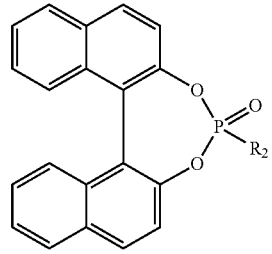

wherein in the above Chemical Formula 1, $R_2$ is $C_1$ to $C_4$ alkyl, phenylmethyl or cyanomethyl.

In exemplary embodiments, $R_2$ is phenylmethyl or cyanomethyl.

The present invention further provides a flame resistant styrenic resin composition comprising: a styrenic resin (A), a polyphenylene ether resin (B) and a phosphonate based compound (C) represented by the above Chemical Formula 1.

In an exemplary embodiment of the present, invention, the flame resistant styrenic resin composition may comprise about 70 to about 99 percent by weight of the styrenic resin (A), about 1 to about 30 percent by weight of the polyphenylene ether resin (B), and about 0.5 to about 30 parts by weight of the phosphonate based compound (C) represented by the above Chemical Formula 1, based on about 100 parts by weight of the base resin (A)+(B).

In an exemplary embodiment of the present invention, the flame resistant styrenic resin composition may further comprise about 1 to about 20 parts by weight of a phosphorus flame retardant (D), based on about 100 parts by weight of the base resin (A)+(B).

The phosphorus flame retardant (D) may be an aromatic phosphorus ester compound (D)-1, a metal salt compound of an alkyl phosphonic acid (D)-2 which has a particle size of less than about 10 or a combination thereof.

In contrast to WO 2008/114858, WO 2008/108485 and US 2008/0227884, the present invention discloses a novel phosphonate compound and a method of making the same which can include adding different derivatives to 1,1'-bi-2-naphthol compound. Further, the present invention provides a thermoplastic resin composition including the novel phosphonate compound.

The present invention now will be described more fully hereinafter in the following detailed description of the invention.

DETAILED DESCRIPTION OF THE INVENTION

Figure 1:
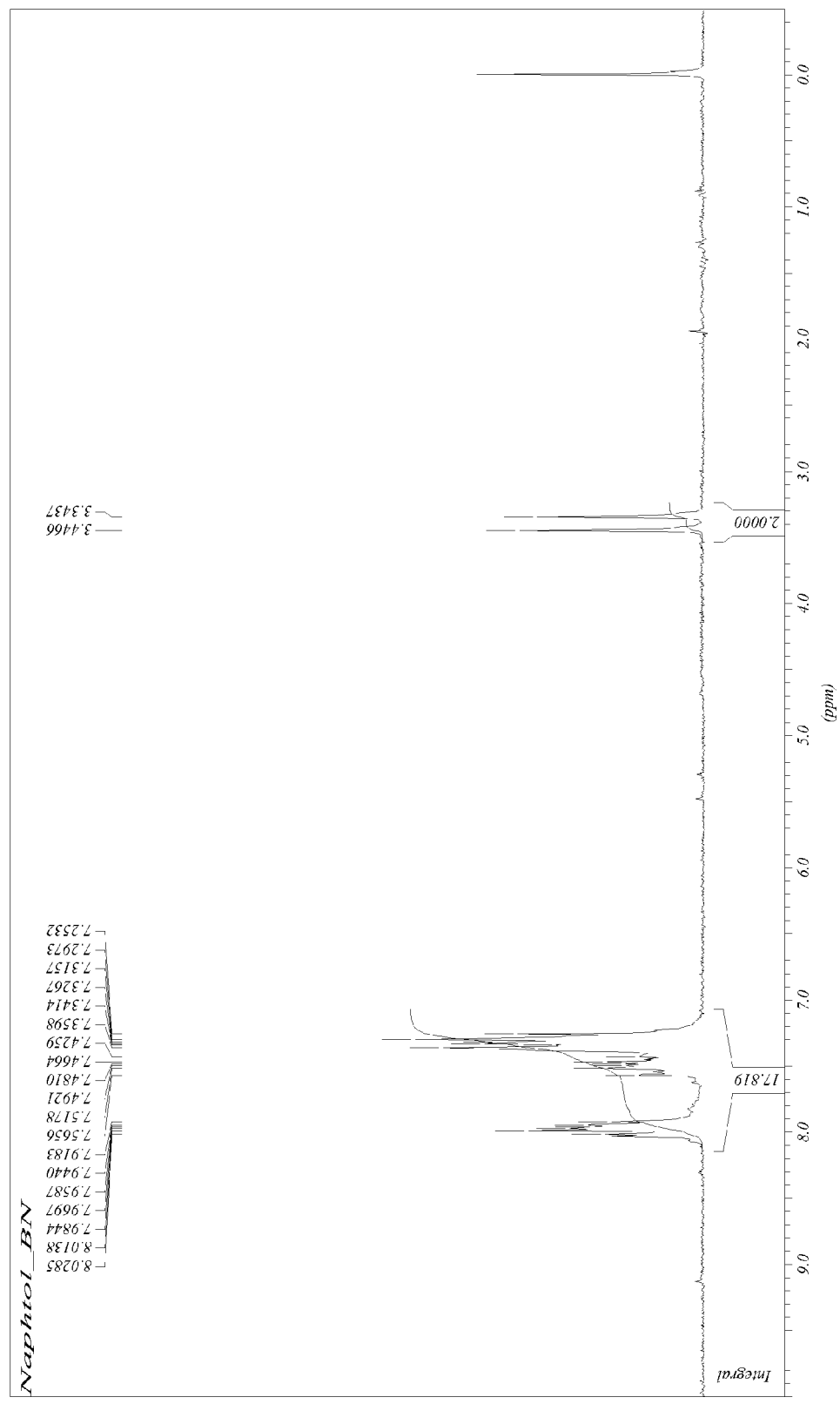
FIG. 1 is a schematic diagram representing the results of $^1$H-NMR analysis of (1,1'-binaphthalene-2,2'-dioxy)phenylmethyl phosphonate according to an exemplary embodiment of the present invention.

The present invention will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

In one exemplary embodiment of the present invention, the present invention provides a phosphonate based compound represented by the following Chemical Formula 1.

[Chemical Formula 1]

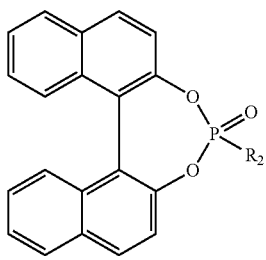

wherein in the above Chemical Formula 1, $R_2$ is $C_1$ to $C_4$ alkyl, phenylmethyl or cyanomethyl.

In exemplary embodiments, $R_2$ is phenylmethyl or cyanomethyl.

The phosphonate based compound represented by the Chemical Formula 1 can be synthesized according to Scheme 1.

[Scheme 1]

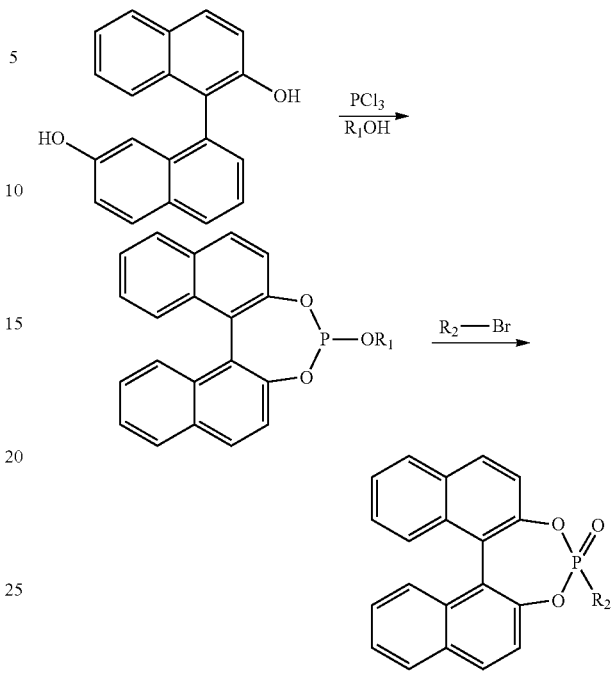

wherein in the above Scheme 1, $R_1$ is $C_1$ to $C_4$ alkyl, and $R_2$ is the same as described above.

(1,1'-binaphthalene-2,2'-dioxy)phenylmethyl phosphonate or (1,1'-binaphthalene-2,2'-dioxy)cyanomethyl phosphonate can be prepared by preparing an intermediate which is prepared by a dechlorination reaction of phosphorus trichloride, aryl-alcohol and ethanol, and reacting the intermediate and a benzylbromide or a bromo acetonitrile.

Preparations of (1,1'-binaphthalene-2,2'-dioxy)phenylmethyl phosphonate and (1,1'-binaphthalene-2,2'-dioxy)cyanomethyl phosphonate are described below.

The (1,1'-binaphthalene-2,2'-dioxy)phenylmethyl phosphonate and (1,1'-binaphthalene-2,2'-dioxy)phenylmethyl phosphonate may prepared as follows. An intermediate such as (1,1'-binaphthalene-2,2'-dioxy)ethyl phosphite can be prepared by stirring about 1 to about 3 equivalence ratio of phosphorus trichloride, for example 1 equivalence ratio, about 1 equivalence ratio of 1,1'-bi-2-naphthol and about 1 equivalence ratio of ethanol, in the presence of nitrogen at room temperature. Then about 1 to about 2 equivalence ratio of benzylbromide or bromo acetonitrile, for example 1 equivalence ratio, can be added to the resultant intermediate and the mixture can be stirred at about 100 to about 150° C.

In another exemplary embodiment of the present invention, the present invention provides a flame resistant styrenic resin composition comprising a styrenic resin (A), a polyphenylene ether resin (B) and a phosphonate based compound (C) represented by Chemical Formula 1.

In an exemplary embodiment of the present invention, the flame resistant styrenic resin composition may comprise about 70 to about 99 percent by weight of the styrenic resin (A), about 1 to about 30 percent by weight of the polyphenylene ether resin (B), and about 0.5 to about 30 parts by weight of the phosphonate based compound (C) represented by the above Chemical Formula 1, based on about 100 parts by weight of the base resin (A)+(B).

In some embodiments, the base resin (A)+(B) can include the styrenic resin (A) in an amount of about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent by weight. Further, according to some embodiments of the present invention, the amount of the styrenic resin (A) can be in a range from about any of the foregoing amounts to about any other of the foregoing amounts.

In some embodiments, the base resin (A)+(B) can include the polyphenylene ether resin (B) in an amount of about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 percent by weight. Further, according to some embodiments of the present invention, the amount of the polyphenylene ether resin (B) can be in a range from about any of the foregoing amounts to about any other of the foregoing amounts.

In some embodiments, the flame resistant styrenic resin composition may include the phosphonate based compound (C) represented by Chemical Formula 1 in an amount of about 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 parts by weight. Further, according to some embodiments of the present invention, the amount of the phosphonate based compound (C) represented by Chemical Formula 1 can be in a range from about any of the foregoing amounts to about any other of the foregoing amounts.

In an exemplary embodiment of the present invention, the flame resistant styrenic resin composition may further comprise about 1 to about 20 parts by weight of a phosphorus flame retardant (D), based on about 100 parts by weight of the base resin (A)+(B). In some embodiments, the flame resistant styrenic resin composition may include the phosphorus flame retardant (D) in an amount of about 1, 2, 3, 4, 5, 6, 7, 8, 9, 10, 11, 12, 13, 14, 15, 16, 17, 18, 19, or 20 parts by weight. Further, according to some embodiments of the present invention, the amount of the phosphorus flame retardant (D) can be in a range from about any of the foregoing amounts to about any other of the foregoing amounts.

Details of each components of the flame resistant styrenic resin composition will be described below.

(A) Styrenic Resin

The styrenic resin (A) that can be used in the resin composition of the present invention can be prepared by mixing a rubber, an aromatic mono-alkenyl monomer, optionally an alkyl ester monomer, and optionally an unsaturated nitrile monomer and thermally polymerizing the mixture or polymerizing the mixture with an initiator Examples of the rubber used in the polymerization of the styrenic resin (A) can include, without limitation, polybutadiene, polyisoprene, styrene-butadiene copolymer, alkyl acrylate rubber and the like, and combinations thereof. The amount of the rubber used can be about 3 to about 30% by weight, for example about 5 to about 15% by weight, based on the total weight of the styrenic resin. In some embodiments, the amount of the rubber can range from about 3, 4, 5, 6, 7, 8, 9, 10, 11, 12, 13, 14, 15, 16, 17, 18, 19, 20, 21, 22, 23, 24, 25, 26, 27, 28, 29, or 30% by weight. Further, according to some embodiments of the present invention, the amount of the rubber can be in a range from about any of the foregoing amounts to about any other of the foregoing amounts.

The monomer for preparing the styrenic resin (A) is an aromatic mono-alkenyl monomer. The amount of the aromatic mono-alkenyl monomer used can be about 70 to about 97% by weight, for example about 85 to about 95% by weight, based on the total weight of the styrenic resin. In some embodiments, the amount of the aromatic mono-alkenyl monomer can range from about 70, 71, 72, 73, 74, 75, 76, 77, 78, 79, 80, 81, 82, 83, 84, 85, 86, 87, 88, 89, 90, 91, 92, 93, 94, 95, 96, or 97% by weight. Further, according to some embodiments of the present invention, the amount of aromatic mono-alkenyl monomer can be in a range of from about any of the foregoing amounts to about any other of the foregoing amounts.

Examples of the aromatic mono-alkenyl monomer can include without limitation styrene, α-methylstyrene, p-methylstyrene, vinyltoluene, 2,4-dimethylstyrene, halogen or C1-C10 alkyl substituted styrene, and the like, and combinations thereof.

Other monomers copolymerizable with the aromatic mono-alkenyl monomer can also be added to the monomers and polymerized to impart properties such as chemical resistance, processability and heat resistance to the polymer. Examples of the other monomers can include without limitation (meth)acrylic alkyl ester compounds, unsaturated nitrile compounds, unsaturated carboxylic acids, maleimide compounds, maleic anhydride, and the like, and combinations thereof.

Examples of the (meth)acrylic acid alkyl esters may include without limitation methacrylic acid $C_1$-$C_8$ alkyl esters, acrylic acid $C_1$-$C_8$ alkyl esters, and combinations thereof. In an exemplary embodiments, the (meth)acrylic acid alkyl esters may include without limitation methacrylic acid methyl ester, methacrylic acid ethyl ester, acrylic acid ethyl ester, acrylic acid methyl ester, methacrylic acid propyl ester, and the like, and combinations thereof.

Examples of the unsaturated nitrile compounds may include without limitation acrylonitrile, methacrylonitrile, and the like, and combinations thereof.

Examples of the unsaturated carboxylic acids may include without limitation acrylic acid, methacrylic acid, and the like, and combinations thereof.

Examples of the maleimide compounds may include without limitation C1-C4 alkyl N-substituted maleimide, phenyl N-substituted maleimide, and the like, and combinations thereof.

These other monomers can be added in an amount of about 0 to about 40 parts by weight per 100 parts by weight of a total weight of the styrenic resin. In some embodiments, the other monomers may not be present in the styrenic resin (A). In some embodiments, the other monomers may be present in the styrenic resin (A), i.e., the styrenic resin (A) may include the other monomers in an amount greater than and/or about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 parts by weight. Further, according to some embodiments of the present invention, the amount of the other monomers can be in a range from about any of the foregoing amounts to about any other of the foregoing amounts.

The styrenic resin (A) can be can be polymerized with heat and no initiator or can be polymerized in the presence of an initiator. Examples of the initiator that can be used may include without limitation organic peroxides such as benzoyl peroxide, t-butyl hydroperoxide, acetyl peroxide and cumene hydroperoxide, azo compounds such as azobisisobutyronitrile, and the like, and combinations thereof.

Polymerization methods for making the styrenic resin (A) can include bulk polymerization, suspension polymerization, emulsion polymerization or a combination thereof.

The average size of rubber particles can range from about 0.1 to about 4.0 μm to optimize physical properties when blending a styrenic resin and a polyphenylene ether resin.

(B) Polyphenylene Ether Resin

The resin composition according to the present invention may employ a polyphenylene ether resin (B) with the styrenic resin (A) as a base resin to further improve flame retardancy and heat resistance.

Examples of the polyphenylene ether resin (B) can include, without limitation, poly(2,6-dimethyl-1,4-phenylene)ether, poly(2,6-diethyl-1,4-phenylene)ether, poly(2,6-dipropyl-1,4-phenylene)ether, poly(2-methyl-6-ethyl-1,4-phenylene)ether, poly(2-methyl-6-propyl-1,4-phenylene)ether, poly(2-ethyl-6-propyl-1,4-phenylene)ether, poly(2,6-diphenyl-1,4-phenylene)ether, copolymer of poly(2,6-dimethyl-1,4-phenylene)ether and poly(2,3,6-trimethyl-1,4-phenylene)ether, copolymer of poly(2,6-dimethyl-1,4-phenylene)ether and poly(2,3,5-triethyl-1,4-phenylene)ether, and the like. These can be used alone or as a combination thereof. In exemplary embodiments, a copolymer of poly(2,6-dimethyl-1,4-phenylene)ether and poly(2,3,6-trimethyl-1,4-phenylene)ether or poly(2,6-dimethyl-1,4-phenylene)ether can be used.

The degree of polymerization of the polyphenylene ether resin (B) is not limited specifically, but can vary depending on factors such as heat-stability or processability of the resin composition. The intrinsic viscosity of the polyphenylene ether resin may be in the range of about 0.2 to about 0.8 as measured in chloroform solvent at 25° C.

In an exemplary embodiment of the present invention, the base resin composition may comprise about 70 to about 99% by weight of the styrenic resin (A) and about 1 to about 30% by weight of the polyphenylene ether resin (B). In exemplary embodiments, the polyphenylene ether resin (B) can be used in an amount of about 15 to about 30% by weight, based on a total weight of the base resin (A)+(B). When the polyphenylene ether resin (B) is used in an amount of less than about 1% by weight, flame retardancy may tend to decrease. In addition when the polyphenylene ether resin (B) is used in an amount of greater than about 30% by weight, processability can be deteriorated.

(C) Phosphonate Based Compound

The phosphonate based compound (C) represented by the above Chemical Formula 1 can be used in an amount of about 0.5 to about 30 parts by weight, for example about 5 to about parts by weight, based on about 100 parts by weight of the base resin comprising the styrenic resin (A) and the polyphenylene ether resin (B).

When the phosphonate based compound (C) represented by the above Chemical Formula 1 is used in an amount of less than about 0.5 parts by weight, flame retardancy tends to decrease. When the phosphonate based compound (C) is used in an amount of greater than about 30 parts by weight, flame retardancy tends to increase but physical properties of the total resin such as mechanical strength can be deteriorated.

[Chemical Formula 1]

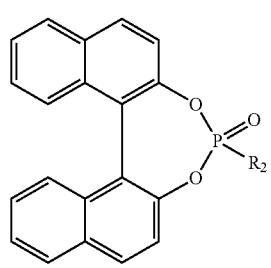

wherein in the above Chemical Formula 1, $R_2$ is $C_1$ to $C_4$ alkyl, phenylmethyl or cyanomethyl.

The phosphonate based compound (C) represented by the above Chemical Formula 1 can be (1,1'-binaphthalene-2,2'-dioxy)phenylmethyl phosphonate or (1,1'-binaphthalene-2,2'-dioxy)cyanomethyl phosphonate.

(D) Phosphorus Flame Retardant

In an exemplary embodiment of the present invention, the flame resistant styrenic resin composition may further comprise a phosphorus flame retardant (D). For example, the phosphorus flame retardant (D) may be an aromatic phosphate ester compound (D)-1, a metal salt compound of an alkyl phosphonic acid (D)-2 which has a particle size of less than about 10 μm, or a combination thereof. The phosphorus flame retardant (D) can be used in an amount of about 1 to about 20 parts by weight, based on about 100 parts by weight of the base resin (A)+(B). When the phosphorus flame retardant (D) is further included, the phosphonate based compound (C) can be used in an amount of about 1 to about 20 parts by weight, based on about 100 parts by weight of the base resin (A)+(B).

In some embodiments, the phosphorus flame retardant (D) may be used in an amount of about 1, 2, 3, 4, 5, 6, 7, 8, 9, 10, 11, 12, 13, 14, 15, 16, 17, 18, 19, or 20 parts by weight. Further, according to some embodiments of the present invention, the amount of the phosphorus flame retardant (D) can be in a range from about any of the foregoing amounts to about any other of the foregoing amounts.

(D)-1 Aromatic Phosphate Ester Compound

The aromatic phosphate ester compound used in the present invention can have a structure represented by the following Formula 2.

[Chemical Formula 2]

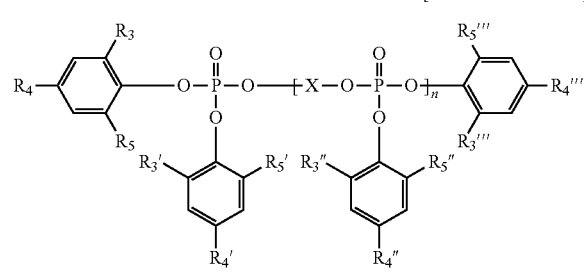

wherein $R_3$, $R_4$, $R_5$, $R_3'$, $R_4'$, $R_5'$, $R_3''$, $R_4''$, $R_5''$, $R_3'''$, $R_4'''$ and $R_5'''$ are each independently hydrogen or $C_1$-C4 alkyl; X is $C_6$-$C_{20}$ aryl or $C_1$-C4 alkyl-substituted $C_6$-$C_{20}$ aryl; and n is an integer of 0 to 4.

X may be a derivative of a dialcohol such as resorcinol, hydroquinol or bisphenol-A.

Where n is 0, examples of the compound represented by Formula 2 can include, without limitation, triphenyl phosphate, tri(2,6-dimethyl)phosphate, and the like, and where n is 1, examples of the compound can include, without limitation, resorcinol bis(diphenyl)phosphate, resorcinol bis(2,6-dimethyl phenyl)phosphate, resorcinol bis(2,4-ditertiary butyl phenyl) phosphate, hydroquinol bis(2,6-dimethyl phenyl)phosphate, hydroquinol bis(2,4-ditertiary butyl phenyl) phosphate, and the like. The aromatic phosphate ester compound (D)-1 can be used alone or in combination thereof.

(D)-2 Metal Salt Compound of Alkyl Phosphonic Acid

The metal salt compound of alkyl phosphonic acid used in the present invention can have a structure represented by the following Formula 3 and have a particle size of less than about 10 μm.

[Chemical Formula 3]

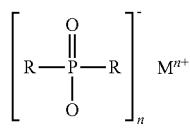

wherein each R is independently $C_1$-$C_6$alkyl, $C_1$-$C_6$ cycloalkyl or $C_6$-$C_{10}$aryl; M is a metal such as Al, Zn, Ca; and n is an integer of 2 or 3.

For example, the two Rs may be same or different. In exemplary embodiments, each R may be independently methyl, ethyl, propyl, butyl or phenyl.

In exemplary embodiments, M may be Al or Zn.

The resin composition of the present invention can be prepared by conventional methods employed in the manufacture of resin compositions. The resin composition according to the present invention may further include one or more additives selected without limitation from plasticizers, heat stabilizers, antioxidants, compatibilizers, light-stabilizers, inorganic additives, pigments, dyes and the like, and combinations thereof. Examples of the inorganic additives may include asbestos, glass fiber, talc, ceramic, sulfate and the like, and combinations thereof. The one or more additives may be used in an amount of less than about 30 parts by weight based on the total weight of the resin composition.

In another embodiment of the present invention, the present invention provides a molded article prepared from the flame resistant styrenic resin composition of the present invention. The molded article may have excellent impact strength and flame resistance and can be environmentally-friendly.

The invention may be better understood by reference to the following examples which are intended for the purpose of illustration and are not to be construed as in any way limiting the scope of the present invention, which is defined in the claims appended hereto.

EXAMPLES AND COMPARATIVE EXAMPLES

Components used in the following examples and comparative examples are as follows.

(A) Non-Halogen Flame Resistant Styrenic Resin Composition (A) Styrenic resin: Rubber-reinforced styrenic resin made by Cheil Industries, Inc. of South Korea (product name: HG-1760S) is used.

(B) Polyphenylene ether (PPE) resin: Poly(2,6-dimethylphenylether) made by Mitsubishi Engineering Plastic Corporation of Japan (product name: PX-100F) is used, and the particle size is several tens of μm in the form of a powder.

(C) Phosphonate based compound represented by the Chemical Formula 1: (1,1'-binaphthalene-2,2'-dioxy)phenylmethyl phosphonate prepared in Preparation Example 1 and (1,1'-binaphthalene-2,2'-dioxy)cyanomethyl phosphonate prepared in Preparation Example 2 are used.

(D)-1 Aromatic Phosphorus Ester Compound: Bis(dimethylphenyl)phosphate bis-phenol A made by DAIHACHI Chemical Industry Co., Ltd. (product name: CR741S) is used.

(D)-2 Metal Salt Compound of Alkyl Phosphonic Acid: Aluminum salt of diethyl phosphonic acid made by Clariant Corporation (product name: Exolit OP930) is used.

Preparation Example 1

Preparation of (1,1'-binaphthalene-2,2'-dioxy)phenylmethyl phosphonate

After injecting phosphorus tri-chloride (137.3 g, 1.0 mol), 1,1'-bi-2-naphthol (286.3 g, 1 mol) and ethanol (46.1 g, 1.0 mol) into a receptacle, the mixture is stirred for 3 hours in the presence of nitrogen at room temperature. After adding benzyl bromide (171.0 g, 1 mol), the temperature of the receptacle is raised to 150° C. and the mixture is stirred for 12 hours in the presence of nitrogen. Then, the temperature of the receptacle is lowered to room temperature and the contents are washed with dimethyl ether, and (1,1'-binaphthalene-2,2'-dioxy)phenylmethyl phosphonate which has a degree of purity of more than about 98% and a yield rate of about 93% is recovered. FIG. 1 represents the results of $^1$H-NMR analysis of (1,1'-binaphthalene-2,2'-dioxy)phenylmethyl phosphonate prepared by the above method.

Preparation Example 2

Preparation of (1,1'-binaphthalene-2,2'-dioxy)cyanomethyl phosphonate

Figure 2:
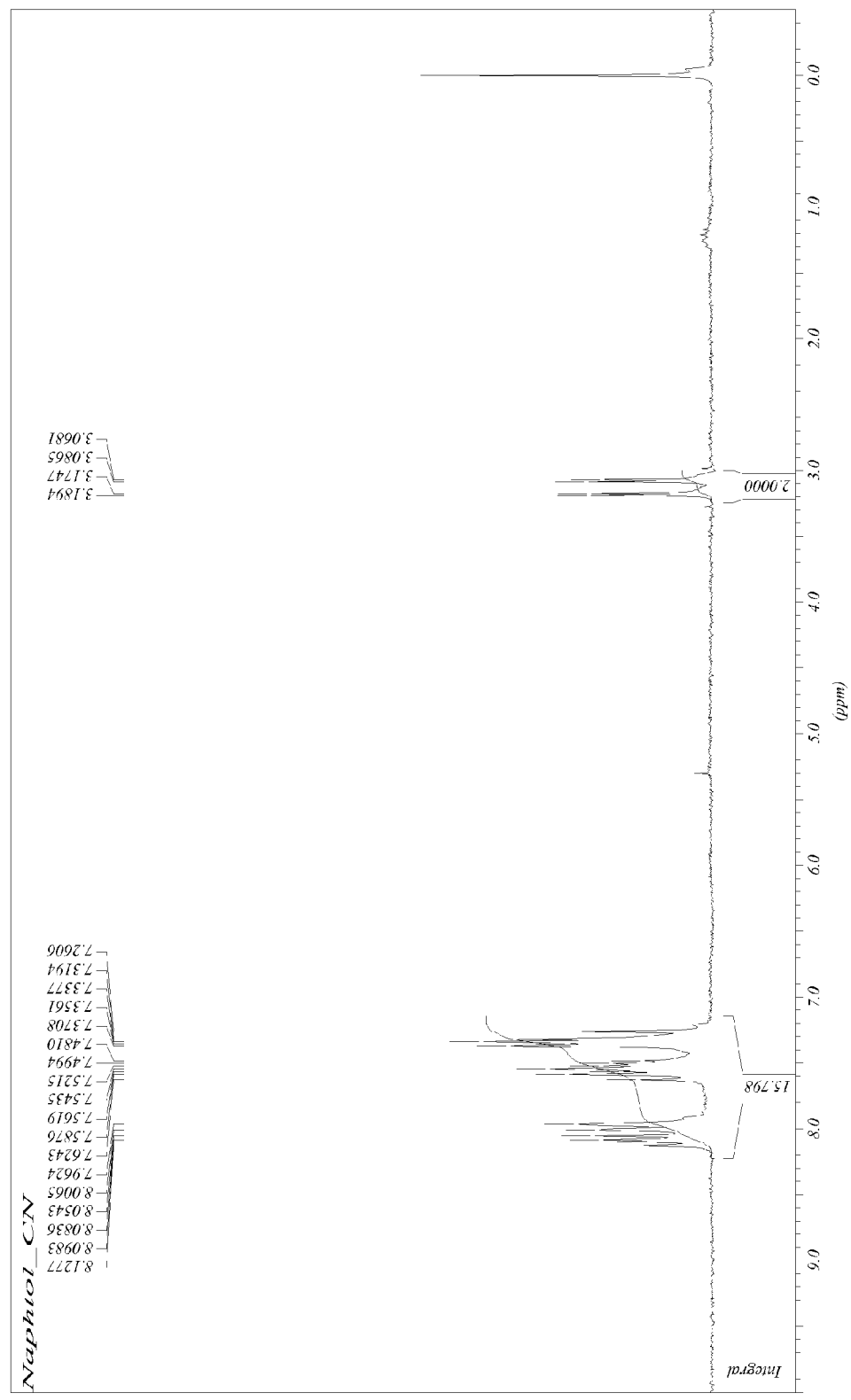
FIG. 2 is a schematic diagram representing the results of $^1$H-NMR analysis of (1,1'-binaphthalene-2,2'-dioxy)cyanomethyl phosphonate according to another exemplary embodiment of the present invention.

After injecting phosphorus tri-chloride (137.3 g, 1.0 mol), 1,1'-bi-2-naphthol (286.3 g, 1 mol) and ethanol (46.1 g, 1.0 mol) into a receptacle, the mixture is stirred for 3 hours in the presence of nitrogen at room temperature. After adding bromo-acetonitrile (119.9 g, 1 mol), the temperature of the receptacle is raised to 150° C. and the mixture is stirred for 12 hours in the presence of nitrogen. Then, the temperature of the receptacle is lowered to room temperature and the contents are washed with dimethyl ether, and (1,1'-binaphthalene-2,2'-dioxy)cyanomethyl phosphonate which has a degree of purity of more than about 98% and a yield rate of about 93% is recovered. FIG. 2 represents the results of 1H-NMR analysis of (1,1'-binaphthalene-2,2'-dioxy)cyanomethyl phosphonate prepared by the above method.

Examples

The components in amounts shown in the following Table 1 are extruded through a conventional extruder at about 240° C. to prepare pellets. After the prepared pellets are dried, the pellets are injected under conditions of a molding temperature of 230° C. and a tool temperature of 50° C. Then, flame resistant samples are prepared. The flame resistance of prepared samples is measured according to UL 94 VB with a thickness of ⅛" and the impact strength is measured according to ASTM D256.

Comparative Examples

Comparative Examples are prepared in the same manner as the Examples above except the Comparative Examples include the components in the amounts shown in the following Table 1. The results are shown in the following Table 1.

TABLE 1

| | Examples | | | | Comparative Examples | | |
|---|---|---|---|---|---|---|---|
| | 1 | 2 | 3 | 4 | 1 | 2 | 3 |
| HIPS | 75 | 75 | 75 | 75 | 75 | 75 | 75 |
| PPE | 25 | 25 | 25 | 25 | 25 | 25 | 25 |
| (1,1'-binaphthalene-2,2'-dioxy)phenylmethyl phosphonate | 5 | 20 | — | — | — | — | — |

TABLE 1-continued

|  | Examples | | | | Comparative Examples | | |
| --- | --- | --- | --- | --- | --- | --- | --- |
|  | 1 | 2 | 3 | 4 | 1 | 2 | 3 |
| (1,1'-binaphthalene-2,2'-dioxy)cyano-methyl phosphonate | — | — | 5 | 20 | — | — | — |
| aromatic phosphorous ester | 15 | — | 15 | — | 15 | 10 | 20 |
| metal salt of alkyl phosphonic acid | — | — | — | — | 5 | — | — |
| UL 94 flame resistance (1/8") | V-1 | V-1 | V-0 | V-1 | V-1 | fail | V-1 |
| Total burning time | 70 | 110 | 37 | 100 | 103 | — | 120 |
| IZOD | 4.0 | 7.5 | 4.2 | 7.6 | 3.4 | 4.5 | 4.7 |

As illustrated by the results set forth in Tables 1, when the (1,1'-binaphthalene-2,2'-dioxy)phenylmethyl phosphonate and (1,1'-binaphthalene-2,2'-dioxy)cyanomethyl phosphonate are used, flame resistance and impact strength are excellent compared to an aromatic phosphorus ester compound.

IZOD results of examples 1 and 3 are superior to that of comparative examples 1 and IZOD results of examples 2 and 4 are also superior to that of comparative examples Therefore, when a phosphonate based compound represented by the following Chemical Formula 1 as a flame retardant, flame retardancy can be excellent and impact strength can also be improved at the same time.

The flame resistant styrenic resin composition including the phosphonate compound of the present invention can have excellent impact strength and flame resistance and is environmentally-friendly.

Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation, the scope of the invention being defined in the claims.

The invention claimed is:

1. A phosphonate based compound represented by the following Chemical Formula 1:

[Chemical Formula 1]

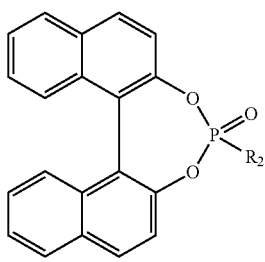

wherein $R_2$ is $C_1$ to $C_4$ alkyl, phenylmethyl or cyanomethyl.

2. The phosphonate based compound of claim 1, wherein $R_2$ is phenylmethyl.

3. The phosphonate based compound of claim 1, wherein $R_2$ is cyanomethyl.

4. A flame resistant styrenic resin composition comprising a styrenic resin (A), a polyphenylene ether resin (B) and a phosphonate based compound (C) represented by the Chemical Formula 1:

[Chemical Formula 1]

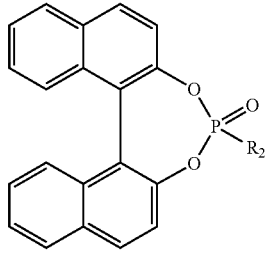

wherein $R_2$ is $C_1$ to $C_4$ alkyl, phenylmethyl or cyanomethyl.

5. The flame resistant styrenic resin composition of claim 4, comprising 70 to 99 percent by weight of the styrenic resin (A), 1 to 30 percent by weight of the polyphenylene ether resin (B), and 0.5 to 30 parts by weight of the phosphonate based compound (C) represented by Chemical Formula 1, based on 100 parts by weight of a base resin (A)+(B).

6. The flame resistant styrenic resin composition of claim 5, further comprising 1 to 20 parts by weight of a phosphorus flame retardant (D) based on 100 parts by weight of a base resin (A)+(B).

7. The flame resistant styrenic resin composition of claim 6, wherein said phosphorus flame retardant (D) comprises an aromatic phosphorus ester compound (D)-1, a metal salt compound of an alkyl phosphonic acid (D)-2 which has a particle size of less than about 10 μm, or a combination thereof.

8. The flame resistant styrenic resin composition of claim 7, wherein said aromatic phosphorus ester compound (D)-1 is represented by the following Chemical Formula 2:

[Chemical Formula 2]

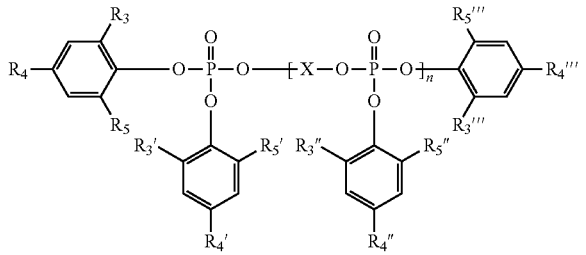

wherein each $R_3$, $R_4$, $R_5$, $R_3'$, $R_4'$, $R_5'$, $R_3''$, $R_4''$, $R_5''$, $R_3'''$, $R_4'''$ and $R_5'''$ is independently H or $C_1$ to $C_4$ alkyl, X is $C_6$ to $C_{20}$ aryl or $C_6$ to $C_{20}$ aryl substituted with $C_1$ to $C_4$ alkyl, and n is an integer ranging from 0 to 4.

9. The flame resistant styrenic resin composition of claim 7, wherein said metal salt compound of alkyl phosphonic acid (D)-2 is represented by the following Chemical Formula 3:

[Chemical Formula 3]

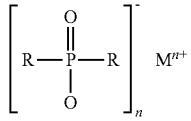

wherein each R is independently $C_1$ to $C_6$ alkyl, $C_1$ to $C_6$ cycloalkyl or $C_6$ to $C_{10}$ aryl, M is Al, Zn, or Ca, and n is an integer of 2 or 3.

10. The flame resistant styrenic resin composition of claim 4, wherein said styrenic resin (A) is prepared by polymerizing a rubber, an aromatic mono-alkenyl monomer, optionally an alkyl ester monomer and optionally an unsaturated nitrile monomer.

11. The flame resistant styrenic resin composition of claim 4, wherein said polyphenylene ether resin (B) comprises poly(2,6-dimethyl-1,4-phenylene)ether, poly(2,6-diethyl-1,4-phenylene)ether, poly(2,6-dipropyl-1,4-phenylene)ether, poly(2-methyl-6-ethyl-1,4-phenylene)ether, poly(2-methyl-6-propyl-1,4-phenylene)ether, poly(2-ethyl-6-propyl-1,4-phenylene)ether, poly(2,6-diphenyl-1,4-phenylene)ether, copolymer of poly(2,6-dimethyl-1,4-phenylene)ether and poly(2,3,6-trimethyl-1,4-phenylene)ether, copolymer of poly(2,6-dimethyl-1,4-phenylene)ether and poly(2,3,5-triethyl-1,4-phenylene)ether or a combination thereof.

12. The flame resistant styrenic resin composition of claim 5, further comprising less than 30 parts by weight of a plasticizer, heat stabilizer, antioxidant, compatibilizer, light-stabilizer, inorganic additive, pigment, dye or a combination thereof based on 100 parts by weight of the base resin (A)+(B).

13. A molded article prepared from the flame resistant styrenic resin composition of claim 4.

* * * * *